United States Patent [19]

Volkwein et al.

[11] 4,102,927

[45] Jul. 25, 1978

[54] PROCESS FOR THE PREPARATION OF 2,4-DINITROANILINE

[75] Inventors: Gert Volkwein, Kelkheim, Taunus; Konrad Baessler, Frankfurt am Main, both of Germany

[73] Assignee: Hoechst Aktiengesellschaft, Frankfurt am Main, Germany

[21] Appl. No.: 713,141

[22] Filed: Aug. 10, 1976

[30] Foreign Application Priority Data

Aug. 16, 1975 [DE] Fed. Rep. of Germany ....... 2536454

[51] Int. Cl.$^2$ ............................................. C07C 85/04
[52] U.S. Cl. ................................................... 260/581
[58] Field of Search ........................... 260/581, 595 A

[56] References Cited

PUBLICATIONS

Sidgwick, "The Organic Chemistry of Nitrogen", p. 143, (1966).

Primary Examiner—Winston A. Douglas
Assistant Examiner—John J. Doll
Attorney, Agent, or Firm—Connolly and Hutz

[57] ABSTRACT 2,4-dinitroaniline is obtained in high yield and quality in a safe reaction by introducing 4-chloro-1,3-dinitrobenzene into at least three-fold stoichiometric amount of aqueous ammonia of a concentration of 15 to 40% by weight at a temperature of 60° to 90° C.

6 Claims, No Drawings

PROCESS FOR THE PREPARATION OF 2,4-DINITROANILINE

The invention relates to a process for preparing 2,4-di-nitroaniline by nucleophilic exchange of the chlorine atom in 2,4-dinitrochloro-benzene against the amino group with the aid of an aqueous ammonia solution.

To prepare this compound, which represents an important intermediate product, numerous methods are described in the literature. The aminating agents used are urea (German Pat. No. 480,343), ammonium acetate (German Pat. No. 376,796) or acetamide (Berichte der Deutschen Chemischen Gesellschaft 32 (1899), 3539), preferably ammonia (in a gaseous state or in an aqueous solution).

According to BIOS FINAL REPORT 1153, page 98, the 4-chloro-1,3-dinitrobenzene is mixed with 125% of the theoretical amount of an aqueous solution containing 5.7% by weight of ammonia. After heating cautiously to 70° C the exchange begins with an exothermic reaction, and the temperature is allowed to increase only up to 120° C. The yield of 2,4-dinitroaniline is 84.3% of the theory, calculated on 4-chloro-1,3-dinitrobenzene; the melting point is between 177° and 179° C.

Better yields are achieved according to U.S. Pat. No. 2,305,573 when heating 4-chloro-1,3-dinitrobenzene with 167% of the theoretical amount of an aqueous solution containing 22% by weight of ammonia with addition of chlorobenzene to 150° C. After working up a yield of 2,4-dinitroaniline of 94.5% of the theory, calculated on 4-chloro-1,3-dinitrobenzene is obtained. The melting point is 178.4° C.

According to both methods a light yellow 2,4-dinitroaniline is obtained which is suitable for the direct preparation of azodyestuffs.

With both working methods all reaction components are introduced into the flask together. When cooling insufficiently the exothermic reaction may cause an uncontrolled increase of the temperature and even an explosion-like decomposition of the reaction mixture. Thus, it is known for example (Chem. Eng. Prog. 67 (1971), 6, 51–57), that in the reaction of nitrochlorobenzene with aqueous ammonia to obtain nitroaniline an explosion has taken place by insufficient cooling. The risk of decomposition of the 2,4-dinitroaniline is considerably increased by the presence of two nitro groups.

If, in order to reduce the risk of explosion in the exchange reaction, the methods described above are modified while maintaining the other conditions by introducing one component and adding the other by pumping at the reaction temperature, the same yields and melting points are obtained approximately, but the 2,4-dinitroaniline formed has a brown color and is not suitable as a diazo component.

It has now been found that a light yellow product suitable as a diazo component is obtained in a practically quantitative yield, if more than 300% of the theoretical amount, preferably 400%, calculated on 4-chloro-1,3-dinitrobenzene, of an aqueous ammonia solution of a concentration of 15 to 40% by weight, preferably 20 to 35%, is placed into the flask and the melted 4-chloro-1,3-dinitrobenzene is added, preferably by pumping, at 60° to 90° C, preferably 70° to 80° C.

This method permits carrying out the exothermic exchange reaction without any risk at relatively low temperatures, which method may be easily controlled at any time by stopping the input of 4-chloro-1,3-dinitrobenzene. The reaction may also be carried out continuously.

If the operation is carried out by introducing first the 4-chloro-1,3-dinitrobenzene and adding the aqueous ammonia solution under otherwise the same conditions, the reaction is only completed after stirring for some time at higher temperature, but dark reaction products are obtained.

Thus, the process of the invention permits preparing 2,4-dinitroaniline in a practically quantitative yield without any risk and with a quality suitable as a diazo component.

The exact method is illustrated by the following Example:

Into an autoclave of stainless steel provided with a blade stirrer, 1200 g (1360 cc) of an aqueous ammonia solution (34% by weight, $d^{15}$:0.884) are introduced and heated to 70° C, whereby the pressure is increased to about 6 atmospheres gauge. Then 680 g (about 420 cc) of molten 4-chloro-1,3-dinitrobenzene (softening point of 49° C) are added by pumping. The pressure decreases to about 3 atmospheres gauge. After stirring for half an hour at 70° C the reaction is completed. Pressure is released from the autoclave and the escaping ammonia is absorbed in water. The reaction mixture is allowed to cool to about 50° C while stirring, suction-filtered, and the filter residue is washed with water until neutral and dried. The yield is 540 g of 2,4-dinitroaniline which is 98.4% of theory. The melting point is 178° C to 179° C. The product has a light yellow color and is suitable as a diazo component without any purification step.

We claim:

1. In a process for the preparation of 2,4-dinitroaniline by reacting 4-chloro-1,3-dinitrobenzene with aqueous ammonia at an elevated temperature and under pressure the improvement comprising introducing at a temperature of 60° to 90° C 4-chloro-1,3-dinitrobenzene into at least 300% of the theoretical amount of an aqueous ammonia solution of a concentration of 15 to 40% by weight.

2. A process as claimed in claim 1, wherein the temperature is 70° to 80° C.

3. A process as claimed in claim 1, wherein at least 400% of the theoretical amount of aqueous ammonia is present at the beginning of the reaction.

4. A process as claimed in claim 1, wherein the aqueous ammonia solution has a concentration of 20 to 35% by weight.

5. A process as claimed in claim 1, wherein the 4-chloro-1,3-dinitrobenzene is continuously pumped into the aqueous ammonia solution.

6. A process as claimed in claim 1, which is performed under autogenous pressure.